United States Patent [19]

Suzuki et al.

[11] Patent Number: 5,922,901

[45] Date of Patent: *Jul. 13, 1999

[54] METHOD FOR PRODUCING DIMERIZATION PRODUCT OF ACRYLONITRILE

[75] Inventors: Yasuhiko Suzuki; Yoshihisa Kiso, both of Yamaguchi, Japan

[73] Assignee: Mitsui Chemicals, Inc., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/793,491

[22] PCT Filed: Jun. 26, 1996

[86] PCT No.: PCT/JP96/01760

§ 371 Date: Feb. 26, 1997

§ 102(e) Date: Feb. 26, 1997

[87] PCT Pub. No.: WO97/01531

PCT Pub. Date: Jan. 16, 1997

[30] Foreign Application Priority Data

Jun. 29, 1995 [JP] Japan .................................... 7-164339

[51] Int. Cl.⁶ .......................... C07C 69/76; C07C 51/10; C08C 19/24
[52] U.S. Cl. .......................... 560/102; 562/406; 525/340
[58] Field of Search .......................... 560/102; 562/406; 525/340

[56] References Cited

U.S. PATENT DOCUMENTS 3,671,569  6/1972  Chabardes et al. .............. 260/465.8 D
4,138,419  2/1979  Arakawa et al. .................. 260/429 R

FOREIGN PATENT DOCUMENTS 559168  9/1993  European Pat. Off. .
3337294  4/1985  Germany .

*Primary Examiner*—Mukund J. Shah
*Assistant Examiner*—Tamthom T. Ngo
*Attorney, Agent, or Firm*—Birch, Stewart, Kolasch & Birch, LLP

[57] ABSTRACT

It is contemplated to provide an industrially adapted method for producing a dimerization product of acrylonitrile, which method is capable of producing a straight chain dimer of acrylonitrile efficiently at a high yield in a simple manner using a highly active catalyst exhibiting superior stability, without suffering from occurrence of difficulty removable by-products. In the method according to the present invention, acrylonitrile is subjected to dimerization in the presence of a ruthenium complex composed of a central atom of ruthenium and ligands including cyclopentadiene or its derivative coordinating thereto. The dimerization product, such as adiponitrile, 1,4-dicyanobutene or 1,4-dicyanobutadiene, is useful as an intermediate for producing hexamethylenediamine and adipic acid, both serving for the starting material of nylon 66, or as an intermediate for producing, for example, an antirusting agent and a vulcanization accelerator for rubbers.

17 Claims, No Drawings

METHOD FOR PRODUCING DIMERIZATION PRODUCT OF ACRYLONITRILE

FIELD OF THE TECHNIQUE

The present invention relates to a method for producing a dimerization product of acrylonitrile, in particular, a straight chain dimer, such as adiponitrile, 1,4-dicyanobutene or 1,4-dicyanobutadiene, which is useful as an intermediate for producing hexamethylenediamine and adipic acid, both to be served for the starting materials of nylon 66, or as an intermediate for producing, for example, an antirusting agent or a vulcanization accelerator for rubbers.

BACKGROUND OF THE TECHNIQUE

As a method for producing adiponitrile or its precursor, namely, 1,4-dicyanobutene or 1,4-dicyanobutadiene, by dimerization of acrylonitrile, there have been proposed techniques, such as the one based on an electrolytic dimerization as given in Japanese Patent Kokai No. 27583/1987, the one based on a reaction using a halogenated ruthenium compound and an organic tin halide in the presence of hydrogen as given in Japanese Patent Kokai No. 9531/1994 and the one based on a reaction using a phosphate catalyst and an aromatic amide compound as given in Japanese Patent Kokai No. 1008/1993. The technique based on an electrolytic dimerization has, however, a problem that the energy cost in the production becomes higher and a special installation is required for the production. In the technique based on the reaction using a halogenated ruthenium compound or a phosphite catalyst, problems undesirable for an industrial production are brought about in, for example, that the reaction velocity is low, that the selectivity of the straight chain dimer is low and that the life of the catalyst is short.

Therefore, the object of the present invention is to provide an industrially acceptable method capable of producing a straight chain dimer of acrylonitrile efficiently at a high yield in a simple manner using a highly active catalyst exhibiting a superior stability, without suffering from occurrence of difficultly removable by-products.

DISCLOSURE OF THE INVENTION

The inventors have found that a straight chain dimer of acrylonitrile can be obtained at a high yield by using, as the dimerization catalyst, a ruthenium complex having ligands including cyclopentadiene or its derivative coordinating to the central ruthenium atom.

Thus, the method for producing a dimerization product of acrylonitrile according to the present invention comprises a step of dimerizing acrylonitrole in the presence of a ruthenium complex composed of a central atom of ruthenium and ligands including cyclopentadiene or its derivative coordinating thereto.

The ruthenium complex to be used according to the present invention serves for the dimerization catalyst and composed of a central atom of ruthenium and ligands coordinating thereto including at least one ligand of cyclopentadiene or its derivative. The ruthenium complex may be present as a polymer of such a ruthenium complex as above.

As the group of derivative of cyclopentadiene, there may be enumerated, for example, cyclopentadienyl, indenyl, fluorenyl and tetrahydroindenyl group, wherein the ring in these groups may have one or more substituent groups or atoms selected among alkyl groups having 1–10 carbon atoms, such as methyl, ethyl, propyl, isopropyl, butyl, octyl and decyl; perhalogeno-alkyl groups having 1–10 carbon atoms, such as perfluoromethyl, perfluoroethyl and perfluorodecyl; aryl groups having 6–14 carbon atoms, such as phenyl, toluyl, mesityl, naphthyl, anthracenyl and biphenyl; alkoxyl groups having 1–6 carbon atoms, such as methoxy, ethoxy, propoxy, isopropoxy, butoxy and phenoxy; and halogen atoms, such as fluorine, chlorine, bromine and iodine.

The ruthenium complex to be used according to the present invention has a high activity with scarce reduction of the activity after a long duty operation and is superior in the stability.

The ruthenium complex to be used according to the present invention may have, in addition to the ligand of cyclopentadiene or its derivative, a further ligand of an oxy-hydrocarbon group as represented by RO (in which R represents a hydrocarbon radical—in the following, a ruthenium complex having a ligand of an oxy-hydrocarbon group is denoted as a type A ruthenium complex) or may have further ligands including an olefin compound having 2–8 carbon atoms, such as ethylene, 2,5-norbonadiene, cyclooctadiene and acrylonitrile, and/or a halogen atom, such as fluorine, chlorine, bromine and iodine (in the following, a ruthenium complex having an olefin compound and a halogeno ligand is denoted as a type B ruthenium complex).

A typical type A ruthenium complex is represented by the following general formula (1)

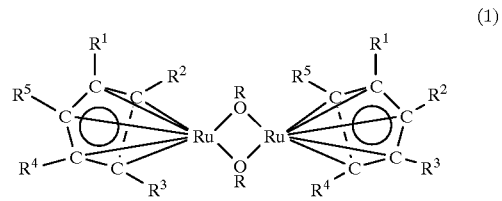

(1)

wherein $R^1$ to $R^5$ each denote, independently of each other, hydrogen atom or an alkyl or aryl group having 1–6 carbon atoms which may combine with another one to form a ring and R denotes a hydrocarbon radical.

A typical type B ruthenium complex is represented by the following general formula (2)

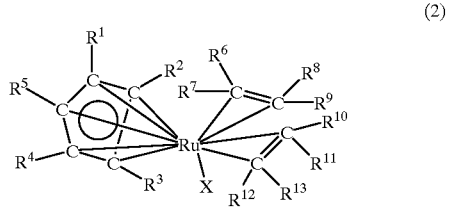

(2)

in which $R^1$ to $R^5$ each denote, independently of each other, hydrogen atom or an alkyl or aryl group having 1–6 carbon atoms which may combine with another one to form a ring, $R^6$ to $R^{13}$ each denote, independently of each other, hydrogen atom, an alkyl or aryl group having 1–6 carbon atoms, cyano group or an ester group which may combine with other ones to form as a whole a diene compound and X is fluorine, chlorine, bromine or iodine.

As the hydrocarbon radical represented by R, there may be enumerated, for example, an alkyl group having 1–10 carbon atoms, such as methyl, ethyl, n-propyl, i-propyl, n-butyl, i-butyl, s-butyl, t-butyl, octyl or decyl; or an aryl group having 6–14 carbon atoms, such as phenyl, toluyl, mesityl, naphthyl, anthracenyl or biphenyl. As a type A ruthenium complex, one having a ligand of an alkoxyl group is preferred.

Beside the above-mentioned ligands of oxy-hydrocarbon group, olefin compound and halogen atom, other ligand(s) may be contained, including a phosphine compound, such as triphenylphosphine or diphenylphosphinoethane; a boron compound, such as tetraphenylboron or methyltriphenylboron; an alkyl group having 1–10 carbon atoms, such as methyl, ethyl, neopentyl, octyl or decyl; an aryl group having 6–14 carbon atoms, such as phenyl, toluyl, mesityl, naphthyl, anthracenyl or biphenyl.

As the ruthenium complex to be used according to the present invention, a type A ruthenium complex, especially a one which has a ligand of alkoxyl group, such as ethoxy group, coordinating to the ruthenium atom, or a type B ruthenium complex is preferred.

According to the present invention, it is permissible to use one single ruthenium complex alone or two or more of such ruthenium complexes in a mixture, wherein the ruthenium complex(es) may desirably be used, in general, in an amount in the range of $1\times10^{-7}$ to 0.5 mole, preferably 0.0001 to 0.1 mole per one mole of acrylonitrile.

In the case of using a type B ruthenium complex, a metal salt and/or a reducing agent may be used together with the ruthenium complex. As the metal salt, there may be enumerated inorganic salts, such as potassium carbonate and sodium carbonate; organic salts, such as sodium acetate; and boron salts, such as sodium tetraphenylborate, sodium tetra (perfluorophenyl)borate and sodium tetra(4-fluorophenyl) borate. These metal salts may be used either alone or in a mixture of two or more of them, wherein the amount thereof may desirably, in general, be in the range of 0.05–30 moles, preferably 0.5–2 moles per one mole of the ruthenium complex.

As the reducing agent, there may be enumerated, for example, organic tin compounds, organic germanium compounds, organic silicium compounds, organic boron compounds, organic aluminum compounds, hydrogenated boron compounds, hydrogenated aluminum compounds, metal hydrides and elementary metals. These reducing agents may be used either alone or in a mixture of two or more of them, wherein the amount thereof may desirably, in general, be in the range of 0.05–30 moles, preferably 0.5–2 moles per one mole of the ruthenium complex.

In the process according to the present invention, it is permitted to incorporate an additive, such as 2-furan carboxylic acid or the like, in an amount of 0.001–1000 moles per one mole of the ruthenium catalyst, in order to improve the selectivity to the straight chain dimer.

According to the present invention, the dimerization may be carried out with or without a solvent, wherein use of a solvent is preferred. As the solvent to be used in the dimerization, there may be enumerated aliphatic alcohols, such as methanol, ethanol, propanol and butanol; halogen-substituted aliphatic alcohols, such as $CF_3CH_2OH$ and $CCl_3CH_2OH$; aromatic alcohols, such as phenol and cresol; organic acids, such as acetic acid and propionic acid; hydrocarbon compounds, such as pentane and hexane; ether compounds, such as tetrahydrofuran and diethyl ether; amine compounds, such as triethylamine and pyrrolidine; and amide compounds, such as dimethylformamide and N-methylpyrrolidone. Among them, aliphatic alcohols are preferable.

These solvents may be used either alone or in a mixture of two or more of them, wherein the amount thereof may, in general, desirably be in the range of 0.001–1,000 parts, preferably 0.1–10 parts by weight per one part by weight of acrylonitrile.

According to the present invention, the dimerization may be carried out in an atmosphere of inert gas, such as argon or the like, or in the co-existence of hydrogen gas. In the case of co-existence of hydrogen gas, the dimerization can be effected, for example, under pressurized hydrogen. Here, the hydrogen partial pressure may desirably be 0.001–10 MPa (gauge), preferably 0.1–3 MPa (gauge). When the dimerization is carried out in the co-existence of hydrogen, the activity of the ruthenium complex becomes higher and the conversion of acrylonitrile is higher, with simultaneous attainment of higher proportions of adiponitrile and 1,4-dicyanobutene in the reaction product with correspondingly reduced proportion of 1,4-dicyanobutadiene. In contrast thereto, when the dimerization is carried out without co-existence of hydrogen, a better selectivity to the straight chain dimers of acrylonitrile is achieved with corresponding reduction of occurrence of by-products.

It is preferable to carry out the dimerization according to the present invention at a temperature of 20–200° C., preferably 80–150° C. The duration of the dimerization may, in general, desirably be from 0.1 to 20 hours, preferbly from 1 to 10 hours.

By effecting the dimerization of acrylonitrile in the manner as given above, straight chain dimers of acrylonitrile, namely, adiponitrile, 1,4-dicyanobutene (as a cis- or trans-isomer) and 1,4-dicyanobutadiene, are obtained together with monomeric products of propionitrile and others. The so-obtained straight chain dimers of acrylonitrile can be used as intermediates for producing the starting materials of nylon 66, i.e. hexamethylenediamine and adipic acid, and for producing antirusting agents, vulcanization accelerators of rubbers and others.

The method according to the present invention can afford to produce a straight chain dimer of acrylonitrile efficiently at a higher yield in a simple manner while suppressing occurrence of difficultly removable by-products, since the dimerization is effected in the presence of a highly active ruthenium complex having superior stability.

THE BEST MODE FOR EMBODYING THE INVENTION

Below, the present invention is described by way of Examples, which should not be regarded as restricting the invention in any respect.

EXAMPLE 1

A stainless steel autoclave having a capacity of 50 ml and equipped with a stirrer and a gas supply valve was caused to replace the internal air with argon, whereupon it was charged with 10 grams (190 mmol) of acrylonitrile and 58.5 milligrams (0.10 mmol) of dimer of pentamethylcyclopentadienylruthenium ethoxide and was supplied with hydrogen gas via the gas supply valve up to a hydrogen partial pressure of 2 MPa, in order to cause dimerization of acrylonitrile at a temperature of 120° C. for 2 hours. The results are summarized in Table 1.

EXAMPLES 2–6

The same procedures as in Example 1 were repeated except that the compound recited in Table 1 was used as the ruthenium complex in an amount of 0.10 mmol in Examples 2–4 and 0.19 mmol in Examples 5–6. The results are summarized also in Table 1.

TABLE 1

| Example No. | Ruthenium complex | AN conversion (mole %) | Dimer yield (mole %) | PN yield (mole %) |
|---|---|---|---|---|
| 1 | [Cp$^1$Ru(OC$_2$H$_5$)]$_2$ | 46 | 27 | 11 |
| 2 | [Cp$^1$Ru(OPr-i)]$_2$ | 37 | 22 | 10 |
| 3 | [Cp$^1$Ru(OBu-t)]$_2$ | 32 | 18 | 10 |
| 4 | [Cp$^1$Ru(OCH$_3$)]$_2$ | 7 | 4 | 2 |
| 5 | Cp$^1$Ru(Ph$_3$P)$_2$Ph | 6 | 3 | 1 |
| 6 | [Cp$^1$RuCl$_2$]$_n$ | 9 | 0.7 | 3 |

(dimerization under co-existence of hydrogen)
Notes:
Cp$^1$ = Pentamethylcyclopentadienyl group [C$_5$(CH$_3$)$_5$]
Pr-i = isopropyl group
Bu-t = tert-butyl group
Ph = Phenyl group
n = a natural number (only for Example 6, the amount of the complex used is given by calculation assuming the group given in the brackets to be one mole, since n of the complex [Cp$^1$RuCl$_2$]$_n$ is variable according to the state of dilution and to the isolation condition)
AN = Acrylonitrile
PN = Propionitrile
Dimer yield = [(moles of dimers formed)/(moles of AN charged)] × 2 × 100

EXAMPLES 7–14

A stainless steel autoclave having a capacity of 50 ml and equipped with a stirrer and a gas supply valve was caused to replace its internal air with argon, whereupon it was charged with 5 grams (95 mmol) of acrylonitrile, 48 μmol of the ruthenium complex given in Table 2 and 19 mmol of the reaction medium given in Table 2 and was supplied with hydrogen gas via the gas supply valve up to a hydrogen partial pressure of 2 MPa, in order to cause dimerization of acrylonitrile at a temperature of 120° C. for 2 hours. The results are summarized in Table 2.

TABLE 2

| Example No. | Ruthenium complex | Reaction medium | AN conv mol % | Dimer yield mol % | PN yd. mol % |
|---|---|---|---|---|---|
| 7 | [Cp$^1$Ru(OC$_2$H$_5$)]$_2$ | Ethanol | 88 | 59 | 24 |
| 8 | [Cp$^1$Ru(OC$_2$H$_5$)]$_2$ | Methanol | 40 | 27 | 11 |
| 9 | [Cp$^1$Ru(OC$_2$H$_5$)]$_2$ | CF$_3$CH$_2$OH | 13 | 9 | 3 |
| 10 | [Cp$^1$Ru(OC$_2$H$_5$)]$_2$ | Phenol | 8 | 5 | 2 |
| 11 | [Cp$^1$Ru(OCH$_3$)]$_2$ | Methanol | 46 | 29 | 12 |
| 12 | [InRu(OC$_2$H$_5$)]$_2$ | Ethanol | 56 | 14 | 35 |
| 13 | [FlRu(OC$_2$H$_5$)]$_2$ | Ethanol | 57 | 13 | 43 |
| 14 | [Cp$^2$Ru(OC$_2$H$_5$)]$_2$ | Ethanol | 14 | 9 | 3 |

(dimerization under co-existence of hydrogen)
Notes:
Cp$^1$ = Pentamethylcyclopentadienyl group [C$_5$(CH$_3$)$_5$]
In = Indenyl group
Fl = Fluorenyl group
Cp$^2$ = Trifluoromethyltetramethylcyclopentadienyl group [C$_5$(CH$_3$)$_4$CF$_3$]
AN conv = Acrylonitrile conversion
PN yd. = Propionitrile yield
Dimer yield = [(moles of dimers formed)/(moles of AN charged)] × 2 × 100

EXAMPLES 15–27

A stainless steel autoclave having a capacity of 50 ml and equipped with a stirrer and a gas supply valve was caused to replace its internal air with argon, whereupon it was charged with 5 grams (95 mmol) of acrylonitrile and 95 μmol of the ruthenium complex given in Table 3 and was supplied with hydrogen gas via the gas supply valve up to a hydrogen partial pressure of 2 MPa, in order to cause dimerization of acrylonitrile at a temperature of 120° C. for 2 hours. The results are summarized in Table 3.

TABLE 3

| Example No. | Ruthenium Complex | Additive Compound | Additive Amount (mole) | AN conversion (mole %) | Dimer yield (mole %) | PN yield (mole %) | Ratio of formed amount |
|---|---|---|---|---|---|---|---|
| 15 | Cp$^1$RuNDCl | — | — | 1 | 0.5 | 0.6 | 41 |
| 16 | Cp$^1$RuNDCl | NaBPh$_4$ | 1 | 13 | 8.3 | 4.1 | 67 |
| 17 | Cp$^1$RuNDCl | NaBPh$_4$ | 3 | 55 | 39.1 | 18.2 | 68 |
| 18 | Cp$^1$RuNDCl | (1*) | 3 | 34 | 23.6 | 8.6 | 73 |
| 19 | Cp$^1$RuNDCl | (2*) | 3 | 1 | 0.2 | 0.3 | 52 |
| 20 | Cp$^1$RuNDCl | (3*) | 3 | 2 | 1.4 | 0.9 | 61 |
| 21 | Cp$^1$Ru(PPh$_3$)$_2$Cl | — | — | 6 | 2.8 | 1.1 | 72 |
| 22 | Cp$^3$RuNDCl | NaBPh$_4$ | 3 | 2 | 1.5 | 0.6 | 71 |
| 23 | Cp$^1$RuNDCl | CH$_3$COOAg | 3 | 32 | 20.0 | 9.1 | 69 |
| 24 | Cp$^1$RuNDCl | LiAlH$_4$ | 10 | 4 | 2.6 | 1.0 | 72 |
| 25 | Cp$^1$RuNDCl | Bu$_3$SnH | 10 | 8 | 5.4 | 2.5 | 68 |
| 26 | Cp$^3$RuNDCl | LiAlH$_4$ | 10 | 9 | 0.5 | 7.1 | 7 |

TABLE 3-continued

| Example No. | Ruthenium Complex | Additive Compound | Amount (mole) | AN conversion (mole %) | Dimer yield (mole %) | PN yield (mole %) | Ratio of formed amount |
|---|---|---|---|---|---|---|---|
| 27 | Cp³RuNDCl | Bu₃SnH | 10 | 7 | 1.5 | 6.0 | 20 |

(Dimerization under co-existence of hydrogen)
Notes:
Cp¹ = Pentamethylcyclopentadienyl group [C₅(CH₃)₅—];
ND = Norbornadiene;
Cp³ = Pentafluoroethyltetramethylcyclopentadienyl group [C₅(CH₃)₄C₂F₅];
Ph = Phenyl group;
Bu = Butyl group;
AN = Acrylonitrile;
PN = Propionitrile;
Dimer yield = [(moles of dimer formed)/(moles of AN charged)] × 2 × 100;
Ratio of formed amount = [(moles of dimer formed)/(moles of dimer formed + moles of PN formed)] × 2 × 100;
Amount of the additive is given in moles per one mole of the complex;

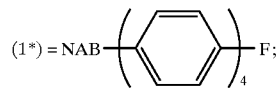

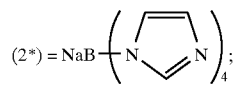

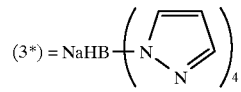

EXAMPLES 28–32

A stainless steel autoclave having a capacity of 50 ml and equipped with a stirrer and a gas supply valve was caused to replace its internal air with argon, whereupon it was charged with 5 grams (95 mmol) of acrylonitrile and 95 μmol of the ruthenium complex and the additive given in Table 4 and dimerization of acrylonitrile was carried out at a temperature of 150° C. for 6 hours under argon atmosphere. The results are summarized in Table 4.

TABLE 4

| Example No. | Ruthenium Complex | Additive Compound | Amount (mole) | Dimer yield (mole %) | PN conversion (mole %) | Ratio of formed amount |
|---|---|---|---|---|---|---|
| 28 | Cp¹RuNDCl | NaBPh₄ | 3 | 4.5 | 2.5 | 64 |
| 29 | Cp¹RuNDCl | NaBPh₄ + i-PrOH | 3 100 | 5.8 | 3.3 | 64 |
| 30 | Cp¹RuNDCl | NaBPh₄ + 2-Fc | 3 100 | 1.2 | 0.4 | 74 |
| 31 | Cp¹RuNDCl | CH₃COOAg + 2-Fc | 3 100 | 4.0 | 0.5 | 88 |
| 32 | Cp¹RuNDCl | — | — | 4.6 | 0.1 | 98 |

(Dimerization without co-existence of hydrogen)
Notes:
Cp¹ = Pentamethylcyclopentadienyl group [C₅(CH₃)₅—);
ND = Norbornadiene;
Ph = Phenyl group;
i-Pr = Isopropyl group;
AN = Acrylonitrile;
PN = Propionitrile;
2-Fc = 2-furan carboxylic acid;
Dimer yield = [(moles of dimer formed)/(moles of AN charged)] × 2 × 100;
Ratio of formed amount = [(moles of dimer formed)/(moles of dimer formed + moles of PN formed)] × 2 × 100;
Amount of the additive is given in moles per one mole of the complex.

We claim:

1. A method for producing dimerization products of acrylonitrile, comprising a step of dimerizing acrylonitrile in the presence of a ruthenium complex comprising a central atom of ruthenium and ligands including cyclopentadiene or its derivative coordinating thereto.

2. The method according to claim 1, wherein the dimerization is carried out in the presence of hydrogen.

3. The method according to claim 1 or 2, wherein the ruthenium complex further comprises an oxy-hydrocarbon group represented by RO coordinating to the central ruthenium atom in which R represents a hydrocarbon radical.

4. The method according to claim 3, wherein the oxy-hydrocarbon group is an alkoxyl group.

5. The method according to claim 4, wherein the alkoxyl group is an ethoxyl group.

6. The method according to claim 1 or 2, wherein the ruthenium complex further comprises a halogen atom and/or an olefin compound coordinating to the central ruthenium atom.

7. The method according to claim 6, wherein the dimerization is carried out in the presence of a metal salt and/or a reducing agent.

8. The method according to claim 1, wherein the dimerized product of acrylonitrile is at least one compound selected from the group consisting of adiponitrile, 1,4-dicyanobutene and 1,4-dicyanobutadiene.

9. The method as claimed in claim 1, wherein the dimerization is carried out in a reaction medium comprising an aliphatic alcohol solvent.

10. The method according to claim 1, wherein said derivative is a cyclopentadienyl, indenyl, fluorenyl or tetrahydroindenyl group, wherein the ring in these groups is unsubstituted, or substituted with one or more of the following groups: an alkyl group having 1–10 carbon atoms, a perhalogenoalkyl group having 1–10 carbon atoms, an aryl group having 6–14 carbon atoms, an alkoxyl group having 1–6 carbon atoms, or a halogen atom.

11. The method according to claim 1, wherein said ruthenium complex is represented by the following formula (1):

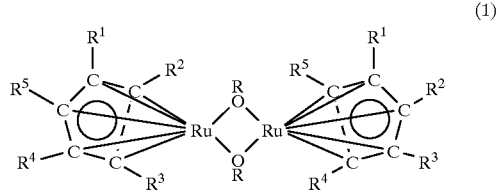

(1)

wherein each of $R^1$ to $R^5$ is, independently of each other, a hydrogen atom, an alkyl or an aryl group having 1–6 carbon atoms, wherein each of $R^1$ to $R^5$ may combine with each other to form a ring; and R is a hydrocarbon radical.

12. The method according to claim 11, wherein R is an alkyl group having 1–10 carbon atoms or an aryl group having 6–14 carbon atoms.

13. The method according to claim 1, wherein said ruthenium complex is represented by the following formula (2):

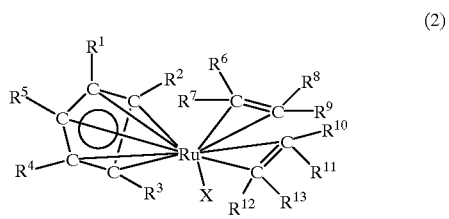

(2)

wherein each of $R^1$ to $R^5$ is, independently of each other, a hydrogen atom, an alkyl group or an aryl group having 1–6 carbon atoms, wherein each of $R^1$ to $R^5$ may combine with each other to form a ring;

each of $R^6$ to $R^{13}$ is, independently of each other, a hydrogen atom, an alkyl group, an aryl group having 1–6 carbon atoms, a cyano group or an ester group, wherein each of $R^6$ to $R^{13}$ may combine with each other to form a diene compound; and X is an olefin compound having 2–8 carbon atoms, a halogen atom, a phosphine compound, a boron compound, an alkyl group having 1–10 carbon atoms, or an aryl group having 6–14 carbon atoms.

14. The method according to claim 1, wherein an amount of the ruthenium complex used is in the range of $1 \times 10^{-7}$ to 0.5 mole per one mole of acrylonitrile.

15. The method according to claim 14, wherein the amount of the ruthenium complex used is in the range of $1 \times 10^{-4}$ to 0.1 mole per one mole of acrylonitrile.

16. The method according to claim 1, wherein said dimerization is carried out at a temperature of 20–200° C.

17. The method according to claim 6, wherein said dimerization is carried out at a temperature of 80–150° C.

* * * * *